United States Patent
Naughton

(10) Patent No.: US 8,588,920 B2
(45) Date of Patent: Nov. 19, 2013

(54) APPARATUS AND METHODS FOR VISUAL PERCEPTION USING AN ARRAY OF NANOSCALE WAVEGUIDES

(75) Inventor: Michael J. Naughton, Norwood, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 506 days.

(21) Appl. No.: 12/744,240

(22) PCT Filed: Nov. 21, 2008

(86) PCT No.: PCT/US2008/084358
§ 371 (c)(1),
(2), (4) Date: May 21, 2010

(87) PCT Pub. No.: WO2009/067668
PCT Pub. Date: May 28, 2009

(65) Prior Publication Data
US 2010/0249877 A1    Sep. 30, 2010

Related U.S. Application Data

(60) Provisional application No. 60/989,577, filed on Nov. 21, 2007.

(51) Int. Cl.
*A61N 1/00* (2006.01)
*A61B 5/04* (2006.01)

(52) U.S. Cl.
USPC ............... 607/54; 607/53; 607/136; 607/137; 600/379

(58) Field of Classification Search
USPC .............. 607/53–54, 136–137; 600/379
See application file for complete search history.

(56) References Cited

U.S. PATENT DOCUMENTS

| | | |
|---|---|---|
| 5,024,223 A | 6/1991 | Chow |
| 5,397,350 A | 3/1995 | Chow et al. |
| 5,556,423 A | 9/1996 | Chow et al. |
| 5,895,415 A | 4/1999 | Chow et al. |
| 6,230,057 B1 | 5/2001 | Chow et al. |
| 6,347,250 B1 * | 2/2002 | Nisch et al. ............... 607/54 |
| 6,389,317 B1 | 5/2002 | Chow et al. |
| 6,427,087 B1 | 7/2002 | Chow et al. |
| 6,611,716 B2 | 8/2003 | Chow et al. |
| 6,755,530 B1 | 6/2004 | Loftus et al. |

(Continued)

OTHER PUBLICATIONS

Dietz, Carl, Insulation of a Carbon Nanotube Interface for Retinal Prostheses, *The National Nanotechnology Infrastructure Network Research Experience for Undergraduates Program, NNIN REU Research Site: Stanford Nanofabrication Facility, Stanford University*, 2004 NNIN REU Research Accomplishments, pp. 38-39 (2004).

(Continued)

*Primary Examiner* — Nicole F Lavert
(74) *Attorney, Agent, or Firm* — Greenberg Traurig, LLP; David J. Dykeman; Roman Fayerberg

(57) ABSTRACT

Nanoscale photovoltaic devices fabricated from nanoscale waveguides that receive, propagate, and convert incident light into electrical neural signals, and methods of using these photovoltaic devices for visual perception are disclosed herein. A visual neuroprosthetic device includes an array of nanoscale waveguides each nanoscale waveguide in the array having a photovoltaic material located between an internal conductor and an external conductor, wherein each nanoscale waveguide receives, propagates, and converts incident light into electrical neural signals.

26 Claims, 12 Drawing Sheets

(56) References Cited

U.S. PATENT DOCUMENTS

| | | |
|---|---|---|
| 6,887,365 B2 | 5/2005 | Naughton |
| 6,958,216 B2 | 10/2005 | Kelley et al. |
| 7,003,354 B2 | 2/2006 | Chow et al. |
| 7,006,873 B2 | 2/2006 | Chow et al. |
| 7,031,776 B2 | 4/2006 | Chow et al. |
| 7,037,943 B2 | 5/2006 | Peyman |
| 7,139,612 B2 | 11/2006 | Chow et al. |
| 7,214,303 B2 | 5/2007 | Naughton |
| 7,462,270 B2 | 12/2008 | Naughton |
| 7,589,880 B2 | 9/2009 | Kempa et al. |
| 7,623,746 B2 | 11/2009 | Naughton et al. |
| 7,634,162 B2 | 12/2009 | Kempa et al. |
| 7,649,665 B2 | 1/2010 | Kempa et al. |
| 2005/0221081 A1 | 10/2005 | Liu et al. |
| 2006/0190058 A1 | 8/2006 | Greenberg et al. |
| 2007/0047056 A1 | 3/2007 | Kempa et al. |
| 2007/0067883 A1* | 3/2007 | Sretavan ............... 977/908 |
| 2007/0081242 A1 | 4/2007 | Kempa et al. |
| 2007/0105240 A1 | 5/2007 | Kempa et al. |
| 2007/0107103 A1 | 5/2007 | Kempa et al. |
| 2007/0137697 A1 | 6/2007 | Kempa et al. |
| 2007/0138376 A1* | 6/2007 | Naughton et al. ............ 250/216 |
| 2007/0142878 A1* | 6/2007 | Krulevitch et al. ............. 607/54 |
| 2007/0235340 A1 | 10/2007 | Naughton |
| 2008/0178924 A1 | 7/2008 | Kempa et al. |

OTHER PUBLICATIONS

Mo, Carbon Nanotubes Stimulate Single Retinal Neurons, http://neurophilosophy.wordpress.com/2006/08/31/carbon-nanotubes-stimulate-single-retinal-neurons/, (Aug. 31, 2006).

Patel, Prachi, Nanotubes Trigger Neurons—Using Carbon Nanotubes as Small Electrodes Might One Day Lead to Safe and Effective Retinal Implants, *Technology Review*—http://www.technologyreview.com/read_article.aspx?id=17389&a=f, (Aug. 31, 2006).

Rybczynski et al., Subwavelength Waveguide for Visible Light, *Applied Physics Letters*, vol. 90, Issue 2, pp. 021104-1-021104-3 (Jan. 8, 2007).

Wang, et al., Neural Stimulation with a Carbon Nanotube Microelectrode Array, *Nano Letters*, vol. 6, No. 9, pp. 2043-2048 (Aug. 26, 2006).

International Search Report based on PCT/US08/84358 mailed Feb. 3, 2009.

* cited by examiner

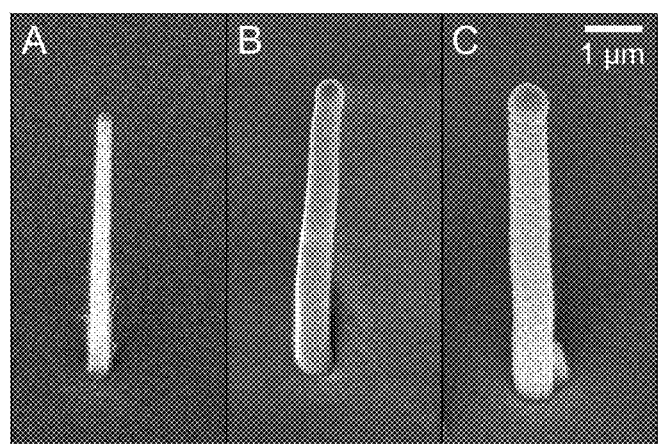
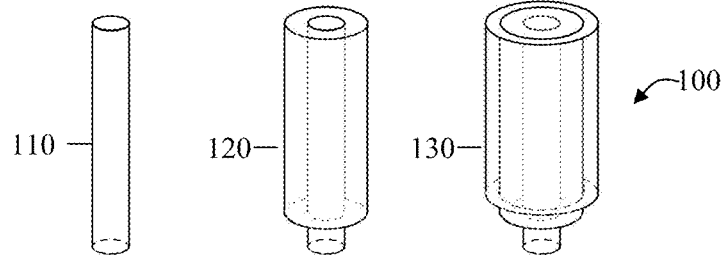
FIG. 1A     FIG. 1B     FIG. 1C

APPARATUS AND METHODS FOR VISUAL PERCEPTION USING AN ARRAY OF NANOSCALE WAVEGUIDES

RELATED APPLICATIONS

This application is a national phase filing under 35 U.S.C. 371 of International Application No. PCT/US2008/084358, filed on Nov. 21, 2008, and claims the benefit of United States Provisional Application Ser. No. 60/989,577, filed on Nov. 21, 2007, the entirety of these applications are hereby incorporated herein by reference for the teachings therein.

FIELD

The embodiments disclosed herein relate to the field of visual neuroprosthetics, and more particularly to the use of nanoscale photovoltaic devices fabricated from nanoscale waveguides that receive, propagate, and convert incident light into electrical neural signals, and methods of using these photovoltaic devices for visual perception.

BACKGROUND

The human eye is like a camera that collects, focuses, and transmits light through a lens to create an image of its surroundings. In a camera, the image is created on film or an image sensor. In the eye, the image is created on the retina, a thin layer of light-sensitive tissue at the back of the eye. When light enters the eye, photoreceptors in the retina absorb the light rays falling on them and convert their energy into electrical impulses, which then travel along the optic nerve to the brain where they are interpreted into visual images. When the photoreceptors in the retina are diseased or damaged, severe or total loss of vision (visual impairment) can occur. Nearly 10,000,000 people around the world suffer from some sort of visual impairment or handicap due to photoreceptor damage.

Until recently, those affected with a visual impairment were left without hope of a cure or even a treatment that would somewhat improve their vision. However, over the last few years, visual neuroprostheses, artificial devices which are inserted in the eye behind or in front of the damaged retinal area, have become available. Electrical stimulation of almost any location along the visual path can evoke phenomenon of perceived vision characterized by "phosphenes". Although the first attempts to restore vision in blind patients date back to the early 20th century, the first mainstream attempts at visual neuroprosthetics took place in the mid-1950s when G. E. Tassiker invented a light-sensitive selenium cell. This cell was to be placed behind the retina of the blind patient and its purpose was to give them the perception of bright sensations. In the 1960s and 1970s, scientists attempted to restore vision by placing electrodes directly onto the surface of the visual cortex. Unfortunately, these implants did not work because they did not provide any useful images. In the 1990s, scientists switched to the idea of the photoreceptive chip. These photoreceptive chips, in theory, should provide information to the healthy neurons residing in the retina, substituting for the damaged photoreceptors. Known devices typically employ arrays of stimulating electrodes powered by photodiodes or microphotodiodes (components that produce an electrical current, voltage potential, or electrochemical potential in response to light) disposed on the epiretinal side (the surface of the retina facing the vitreous cavity) or the subretinal side (the underneath side) of the retina.

There are many limitations with current photoreceptive chips. First, the number of electrodes that come into contact with the neural tissue or ganglion/horizontal cells is too small to function as the tissue naturally would. Second, the electrodes used in the implants are prone to rejection and they tend to decline in performance over time. Thus there is a need in the art for a photoreceptive chip that is biocompatible, flexible, and mimics the natural photoreceptor density of the retina, thus providing a high level of visual acuity.

SUMMARY

Nanoscale photovoltaic devices fabricated from nanoscale waveguides that receive, propagate, and convert incident light into electrical neural signals, and methods of using these photovoltaic devices for visual perception are disclosed herein. According to aspects illustrated herein, there is provided a visual neuroprosthetic device that includes an array of nanoscale waveguides, each nanoscale waveguide in the array having a photovoltaic material located between an internal conductor and an external conductor, wherein each nanoscale waveguide receives, propagates, and converts incident light into electrical neural signals.

According to aspects illustrated herein, there is provided a method of visual perception that includes providing a visual neuroprosthetic device comprising an array of nanoscale waveguides, each nanoscale waveguide in the array having a photovoltaic material located between an internal conductor and an external conductor; implanting the visual neuroprosthetic device into an eye by engaging the device with a retina; receiving incident light on the array of nanoscale waveguides of the visual neuroprosthetic device; propagating the incident light into the array of nanoscale waveguides of the visual neuroprosthetic device; converting the incident light into an electrical neural signal; transferring the electrical neural signal to cells of the retina; and sending the electrical neural signal to a brain to create a visual image.

BRIEF DESCRIPTION OF THE DRAWINGS

The presently disclosed embodiments will be further explained with reference to the attached drawings, wherein like structures are referred to by like numerals throughout the several views. The drawings are not necessarily to scale, the emphasis having instead been generally placed upon illustrating the principles of the presently disclosed embodiments.

FIG. 1A, FIG. 1B, and FIG. 1C each show a schematic view and an exemplary view of a single coaxial nanoscale waveguide of the presently disclosed embodiments. FIG. 1A shows a schematic view and an exemplary view of a carbon nanotube as an internal electrode of the nanoscale waveguide. FIG. 1B shows a schematic view and an exemplary view of the carbon nanotube after being coated with a photovoltaic material. FIG. 1C shows a schematic view and an exemplary view of the photovoltaic coated carbon nanotube after being surrounded with a metal material acting as an external electrode.

FIG. 2A shows an array of nanoscale waveguides on a substrate, where an external electrode of each nanoscale waveguide is a continuous metallic coating. FIG. 2B shows an array of coaxial nanoscale waveguides on a substrate, where an external conductor of each nanoscale waveguide is a local metallic coating that coaxially surrounds each photovoltaic coated carbon nanotube. FIG. 2C shows the array of coaxial nanoscale waveguides from FIG. 2B having a mechanical stabilizing material, such as spin-on-glass.

FIG. 3A shows a diagram of the main parts of the human eye, including a retina. FIG. 3B shows a cross-sectional view of the retina.

FIG. 6A shows a visual prosthetic device with an array of coaxial nanoscale waveguides present on a rectangular shaped substrate. FIG. 6B shows a visual prosthetic device with an array of coaxial nanoscale waveguides present on a circular shaped substrate. FIG. 6C shows a visual prosthetic device with an array of coaxial nanoscale waveguides without a supporting substrate.

Figure 2A:
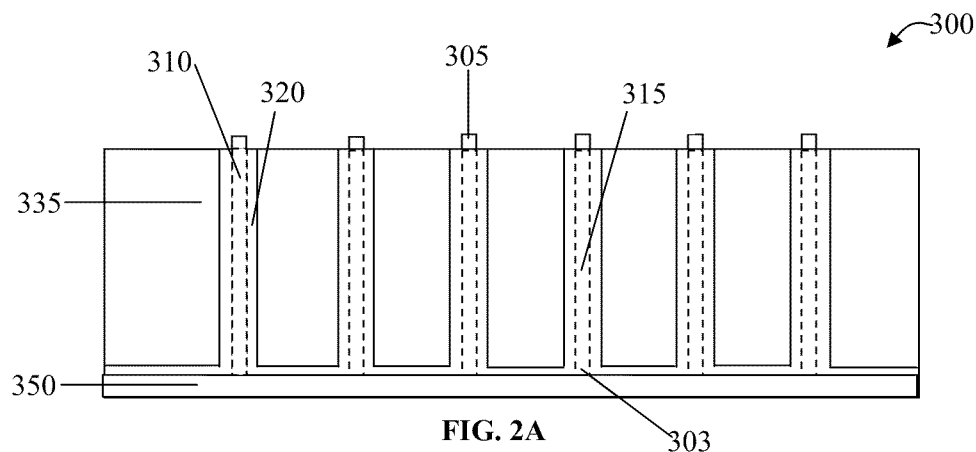
FIG. 2A, FIG. 2B, and FIG. 2C show schematic views of arrays of nanoscale waveguides of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The embodiments disclosed herein relate to the field of visual neuroprosthetics, and more particularly to the use of nanoscale photovoltaic (PV) devices fabricated from nanoscale waveguides that are able to receive, propagate, and convert incident light into electrical neural signals, and methods of using these PV devices for visual perception. When the nanoscale PV devices of the presently disclosed embodiments are placed in a retina, the converted electrical neural signals are transferred to cells of the retina where they travel through optic nerve fibers to the brain and are interpreted as visual images. The nanoscale waveguides of the presently disclosed embodiments have a photovoltaic material located between an internal metallic electrode and an external metallic electrode. In an embodiment, the internal electrode acts as an optical antenna with an impedance-matched transmission line.

The following definitions are used to describe the various aspects and characteristics of the presently disclosed embodiments.

As referred to herein, "nanoscale waveguides", "nanowires", "nanotubes", "carbon nanotubes", "nanopillars" and "nanorods" are used interchangeably. These terms primarily refer to material structures having sizes, e.g., characterized by their largest dimension, in a range of a few nanometers (nm) to about a few microns (μm). In particular, the material comprising the nanostructure need not be carbon.

As referred to herein, "nanoscale" refers to distances and features below about 5000 nanometers (one nanometer equals one billionth of a meter).

As referred to herein, "single-walled carbon nanotubes" (SWCNTs) include one graphene sheet rolled into a cylinder. "Double-walled carbon nanotubes" (DWCNTs) include two graphene sheets in parallel, and those with multiple sheets (typically about 3 to about 30) are "multi-walled carbon nanotubes" (MWCNTs).

As referred to herein, carbon nanotubes are "aligned" wherein the longitudinal axis of individual tubules are oriented in a plane substantially parallel to one another.

As referred to herein, a "tubule" is an individual CNT or nanopillar.

As referred to herein, nanopillars have a "uniform length" wherein the length of individual nanopillars are substantially the same length relative to one another. Depending on preparation conditions used, the height of a nanopillar in an array can be varied in height by about 10% to about 50%. Alternatively, height uniformity is accomplished by performing additional mechanical polish steps. In an embodiment, the nanopillars have a uniform length from about 1 to about 20 micrometers (μm). In an embodiment, the nanopillars have a uniform length from about 5 to about 10 micrometers (μm). In an embodiment, the nanopillars have an average length of about 10 micrometers (μm).

As referred to herein "density" or "site density" denotes units of nanoparticles or nanopillars per centimeter squared (cm$^{-2}$). Site density relates the spacing distance between individual nanopillars in an array. For example, a site density of about 1×10$^6$ cm$^{-2}$ corresponds to a spacing distance of about 10 micrometers (μm). In an embodiment, the spacing distance between individual nanopillars in the array is from about 100 nm to about 10 μm.

As referred to herein "high site density" is a large number of nanopillar units per centimeter squared (cm$^{-2}$). Typically a high site density refers to a number greater than about 1×10$^{12}$ cm$^{-2}$.

As referred to herein "low site density" is a small number of nanopillar units per centimeter squared (cm$^{-2}$). Typically a low site density refers to a number less than or equal to about 1×10$^{12}$ cm$^{-2}$.

The term "linear CNTs" as used herein, refers to CNTs that do not contain branches originating from the surface of individual CNT tubules along their linear axes.

The term "linear nanopillars" as used herein, refers to nanopillars that do not contain branches originating from the surface of individual nanopillars along their linear axes.

The term "array" as used herein, refers to a plurality of nanoscale waveguides or nanopillars or CNT tubules that are proximal to one another.

As referred to herein, the "aspect ratio" of a nanopillar is the ratio of nanopillar length and nanopillar diameter.

As referred to herein, a "coaxial nanoscale waveguide" refers to a nanoscale waveguide which consists of a cylindrical internal conductor, surrounded by a semiconductor spacer, surrounded by a cylindrical external conductor. In an embodiment, the coaxial nanoscale waveguide has an internal metallic electrode, a photovoltaic spacer, and an external metallic electrode. The metals or their surfaces may be composed of the same or different metal materials, or heavily-doped semiconductors. Transmission of electromagnetic energy inside the coaxial nanoscale waveguide is wavelength-independent and happens in transverse electromagnetic (TEM) mode. TEM waves are efficiently propagated in the space in between the two electrodes. Some of these metals could be transparent to the guided radiation.

As referred to herein, "transverse electromagnetic (TEM)" refers to an electromagnetic mode in a transmission waveguide for which both the electric and magnetic fields are perpendicular to the direction of propagation. Other possible modes include but are not limited to transverse electric (TE), in which only the electric field is perpendicular to the direction of propagation, and transverse magnetic (TM), in which only the magnetic field is perpendicular to the direction of propagation.

As referred to herein, a "non-metallic material" is any non-conductive material suitable for depositing a metallic layer thereupon. Examples of "non-metallic material" polymers include but are not limited to, silicon, silica, glass, alumina, quartz, polymer and graphite. Examples of polymers include but are not limited to, polyvinyl chloride (PVC), polyacrylate (PA), polypropylene (PP), polymethylmethacrylate (PMMA), polycarbonate (PC) polyethylene (PE) and thermoset plastics. In an embodiment, the non-metallic material is glass.

As referred to herein, a "conductor" can be a metal, metal alloy, mixture thereof, a polymer, or a doped crystalline semiconductor. Examples of metallic conductors include, but are not limited to, chromium (Cr), molybdenum (Mo), tungsten (W), ruthenium (Ru), copper (Cu), silver (Ag) and gold (Au). In an embodiment, the metallic conductor is chromium (Cr). In an embodiment, the conductor is a conducting polymer. In an embodiment, the conductor is doped crystalline silicon.

As referred to herein, a "catalytic transition metal" can be any transition metal, transition metal alloy or mixture thereof. Examples of a catalytic transition metals include, but are not limited to, nickel (Ni), silver (Ag), gold (Au), platinum (Pt), palladium (Pd), iron (Fe), ruthenium (Ru), osmium (Os), cobalt (Co), rhodium (Rh) and iridium (Ir). In an embodiment, the catalytic transition metal comprises nickel (Ni). In an embodiment, the catalytic transition metal comprises iron (Fe). In an embodiment, the catalytic transition metal comprises cobalt (Co).

As referred to herein, a "catalytic transition metal alloy" can be any transition metal alloy. Preferably, a catalytic transition metal alloy is a homogeneous mixture or solid solution of two or more transition metals. Examples of a catalytic transition metal alloy include, but are not limited to, a nickel/gold (Ni/Au) alloy, nickel/chromium (Ni/Cr) alloy, iron/chromium (Fe/Cr) alloy, and a cobalt/iron (Co/Fe) alloy.

"Pulse-Current Electrochemical Deposition" (PCED) is an electrochemical deposition process which utilizes a modulated current waveform (a current pulse). PCED can be used to achieve superior leveling of the deposit, and to minimize porosity and contamination. PCED is performed by applying a constant current pulse by using a current source and a voltage source. Both the current source and the voltage source are controlled by any suitable means known in the art including analog and digital controller devices. In an embodiment, the current source and the voltage source is controlled by a computer.

As referred to herein, a "working electrode" is a metallic coated non-metallic substrate for use in depositing a catalytic transition metal. In an embodiment, the working electrode is a chromium (Cr) coated silicon (Si) wafer. The chromium (Cr) coating provides a flat, conductive and defect free surface on the silicon (Si) wafer. A method of preparing a chromium (Cr) coated silicon (Si) wafer comprises sputtering a layer of chromium (Cr) on a silicon (Si) wafer. In an embodiment, the sputtering method is magnetron sputtering.

As referred to herein, a "counter electrode" is any suitable electrically-conductive metal. In an embodiment, the counter electrode comprises a noble metal. Examples of suitable noble metals include, but are not limited to, gold (Au), platinum (Pt) and iridium (Ir). In an embodiment, the counter electrode is gold (Au) plate.

As referred to herein, an "electrolytic solution" comprises a transition metal salt and a mineral acid. In an embodiment, the transition metal salt is a transition metal sulfate. In an embodiment, the transition metal sulfate is nickel sulfate ($NiSO_4$). Examples of suitable mineral acids include but are not limited to boric acid ($H_3BO_3$), nitric acid ($HNO_3$), hydrochloric acid (HCl) and sulfuric acid ($H_2SO_4$). In an embodiment, the electrolytic solution is weekly acidic. In an embodiment, the mineral acid is boric acid ($H_3BO_3$). In an embodiment, the electrolytic solution comprises 0.01 M nickel sulfate ($NiSO_4$) and 0.01 M boric acid ($H_3BO_3$) in double distilled water.

CNTs can be grown by any suitable method known in the art. For example, CNTs can be grown by any chemical vapor deposition (CVD) method. In CVD, gaseous mixtures of chemicals are dissociated at high temperature (for example, $CO_2$ into C and $O_2$). This is the "CV" part of CVD. Some of the liberated molecules may then be deposited on a nearby substrate (the "D" in CVD), with the rest pumped away. Examples of CVD methods include but are not limited to, "plasma enhanced chemical vapor deposition" (PECVD), "hot filament chemical vapor deposition" (HFCVD), and "synchrotron radiation chemical vapor deposition" (SRCVD). CNT tubules with substantially improved alignment can be obtained by inclusion of a plasma during the CNT growth process. In an embodiment the CNTs are grown from the catalytic transition metal microparticles by a PECVD process.

As referred to herein, a "promoter gas" can be a substance that is a gaseous compound at the reaction temperatures, and preferably comprises a non-carbon gas such as ammonia, ammonia-nitrogen, hydrogen, thiophene, or mixtures thereof. The promoter gas of the presently disclosed embodiments may be diluted by mixing it with a diluent gas, which are primarily unreactive, oxygen-free gases, such as for example, hydrogen, helium, nitrogen, argon, neon, krypton, xenon, hydrogen sulfide, or combinations thereof. In an embodiment, the promoter gas is hydrogen for a reaction temperature maintained at less than about 700° C. In an embodiment, the promoter gas is chosen from ammonia, hydrogen, nitrogen, or any combination thereof for a reaction temperature greater than or equal to about 700° C. The promoter gas can be introduced into the reaction chamber of the reaction apparatus (e.g. the CVD reaction chamber) at any stage of the reaction process. In an embodiment, the promoter gas is introduced into the reaction chamber either prior to or simultaneously with the carbon source gas.

As referred to herein, a "carbon source gas" of presently disclosed embodiments can be saturated, unsaturated linear branched or cyclic hydrocarbons, or mixtures thereof, that are in either in the gas or vapor phase at the temperatures at which they are contacted with the catalyst substrate material (reaction temperature). Carbon source gases include, but are not limited to, methane, propane, acetylene, ethylene, benzene, or mixtures thereof. In an embodiment, the carbon source gas for the synthesis of linear CNTs is acetylene.

Nanopillars can be grown by any suitable method known in the art. For example, electron beam lithography can be used to define etch sites in a metal or doped silicon wafer which, after deep reactive ion etching, yield arrays of vertically-aligned nanopillars. Other processes known in the art can be use, such as nanoimprint lithography, or electrodeposition into pores of anodize aluminum oxide, followed by chemical dissolution of the oxide.

As referred to herein, an "optical signal" refers to any electromagnetic radiation pulse including gamma rays, X-rays, ultraviolet light, visible light, infrared, microwaves, radio waves (ULF, VLF, LF, MF, HF, long, short, HAM, VHF, UHF, SHF, EHF), cosmic microwave background radiation and other forms of radiation of the electromagnetic spectrum.

As referred to herein, "visible light" refers to light which is detectable by the eye. Visible light consists of wavelengths ranging from approximately 800 nanometer ($8.00 \times 10^{-7}$ m) down to approximately 350 nanometer ($3.50 \times 10^{-7}$ m).

As referred to herein, a "visual impairment" refers to a disease or disorder of the eye including, but not limited to, age-related macula degeneration (AMD), cone-rod dystrophy (CORD), retinitis pigmentosa, choroidal disease, long-term retinal detachment, diabetic retinopathies, Stargardt's disease, choroideremia, Best's disease, blindness due to outer retinal layer damage, and rupture of the choroid. The visual prosthetic devices of the presently disclosed embodiments can be used for diseases where photoreceptors are damaged but the optic nerve and the connections to the brain are still intact.

FIG. 1A, FIG. 1B, and FIG. 1C each show a schematic view and an exemplary view of a single coaxial nanoscale waveguide 100 of the presently disclosed embodiments. The schematic views show the three major layers of the coaxial nanoscale waveguides, an internal metallic electrode 110, a spacer which is a photovoltaic material (PV) 120, and an external metallic electrode 130. The exemplary views were taken using a scanning electron microscope (SEM) at a 30 degree angle to the sample surface.

FIG. 1A shows a schematic view and an exemplary view of the linear internal metallic electrode 110. In the embodiment depicted in FIG. 1A, the internal metallic electrode 110 is a carbon nanotube. The average length of the carbon nanotube 110 is about 5 to about 6 µm. The diameter of the carbon nanotube 110 may range from about 1 nm to about 600 nm.

FIG. 1B shows a schematic view and an exemplary view of the carbon nanotube 110 after being coated with the PV material 120. In an embodiment, the PV material 120 is aluminum oxide ($Al_2O_3$). The thickness of the PV material 120 may range from about 1 nm to about 600 nm. In an embodiment, the thickness of the PV material 120 is about 100 nm.

FIG. 1C shows a schematic view and an exemplary view of a nanoscale waveguide, where the external electrode 130 surrounds the PV coated carbon nanotube. In an embodiment, the external electrode 130 is chromium. The thickness of the external electrode 130 may range from about 10 nm to about 1000 nm. In an embodiment, the thickness of the external electrode 130 is about 150 nm.

Figure 2B:
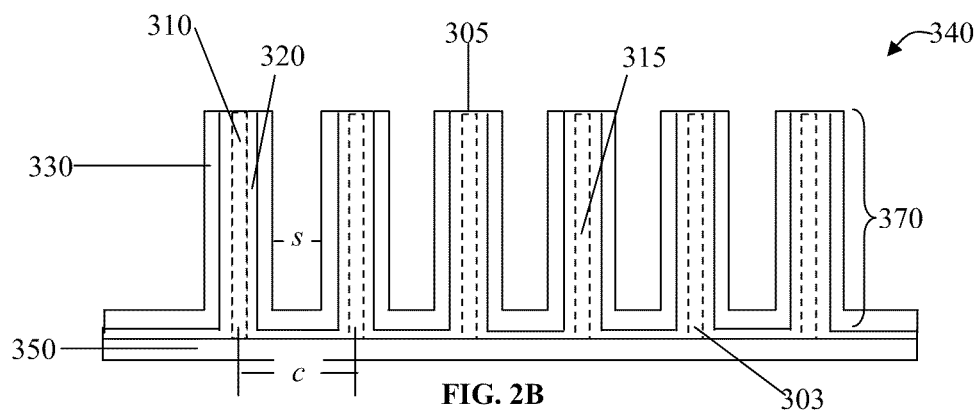
Figure 2C:
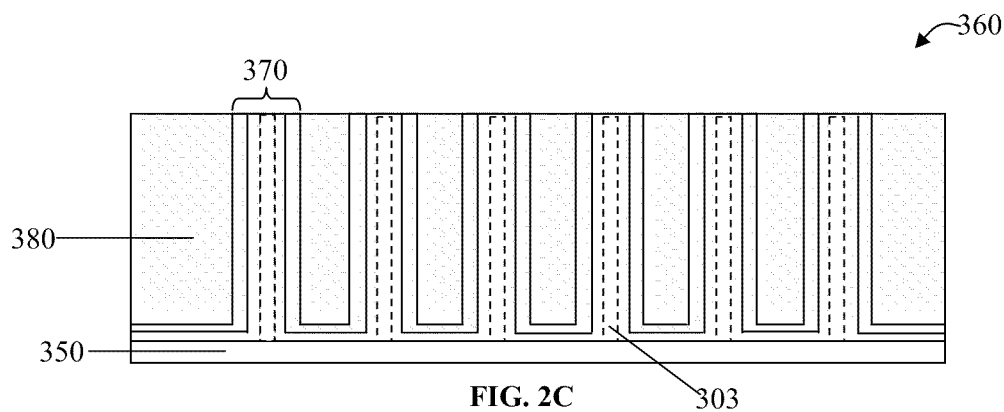

The main components of an embodiment of a nanoscale photovoltaic (PV) device of the present disclosure are shown generally in FIG. 2A, FIG. 2B and FIG. 2C. In the embodiment depicted in FIG. 2A, a PV device 300 includes an array of internal metallic electrodes (nanopillars) 310 that penetrate a metallic film 335 through cylindrical channels filled with a photovoltaic material 320. In the embodiments shown in FIG. 2A, FIG. 2B and FIG. 2C, the internal metallic electrodes 310 are carbon nanotubes or nanofibers. In an embodiment, each nanopillar 310 has at least one optical nano-antenna 303, 305 with an impedance-matched transmission line (TL) 315. In an embodiment, no antenna is employed. In the embodiment shown in FIG. 2A, a nano-antenna extends beyond a top surface of the device, as shown in the nano-antenna 305, and a nano-antenna exists at a bottom surface of the device, as shown in the nano-antenna 303. The TL 315 allows for propagation of external radiation with a wavelength exceeding the perpendicular dimensions of the carbon nanotube 310. The nano-antennas 303, 305 of the presently disclosed embodiments are broadband resonators having large aspect ratios, that is the length of the nano-antenna is much larger than the diameter of the nano-antenna. The bandwidth of the nano-antenna may be tuned to cover the entire solar spectrum. The nano-antenna is capable of receiving and transmitting electromagnetic radiation in the visible range of frequencies. Examples of photovoltaic materials 320 include, but are not limited to, amorphous, nanocrystalline, or microcrystalline silicon, other inorganic PV semiconductors, organic PV, polymeric PV, or other materials known to those skilled in the art.

The nanopillars 310 in the array are grown on a metallic or metal-coated non-metallic substrate 350 to which catalytic transition metal microparticles have been deposited. In an embodiment, the metal-coated non-metallic substrate 350 is removed once the PV device 300 is fabricated, leaving a flexible PV device. In an embodiment, the substrate 350 is transparent to visible light and is present on the PV device 300 and provides support to the array of nanoscale waveguides. The nanopillars 310 may be aligned in rows or unevenly distributed on the substrate 350. The substrate 350 may be transparent. The substrate 350 may be composed of a polymer, glass, ceramic material, carbon fiber, glass fiber or combinations thereof. Those skilled in the art will recognize that the substrate 350 may be other materials known in the art and be within the spirit and scope of the presently disclosed embodiments.

The nanopillars in the array may be grown on either flexible or nonflexible substrates. Flexible substrates may include flexible semiconductors, such as sufficiently thin silicon and plastics, such as sufficiently thin polypropylene, PMMA (poly(methyl methacrylate)), PDMS (polydimethylsiloxane), SU-8, flexible metals, such as sufficiently thin aluminum, or other materials known to those skilled in the art. Nonflexible substrates may include insulators such as glass, semiconductors such as silicon, metals such as aluminum, plastics such as polypropylene, or other materials known to those skilled in the art. In an embodiment, nonflexible substrates may be biocompatible or may be capable of being coated with a biocompatible material. In an embodiment, nonflexible substrates may be tolerant of nanocoax array fabrication processes, such as thermal and chemical stability.

In an embodiment, a PV device of the present disclosure is fabricated by growing an array of nanoscale waveguides on a flexible substrate. The array of nanoscale waveguides includes an internal conductor (i.e., a nanopillar), a photovoltaic material, and an external conductor. In an embodiment, a method of fabricating a PV device by growing an array of nanoscale waveguides on a flexible substrate includes curing (solidifying) the nanoscale waveguides using, for example, thermal or ultra-violet (UV) exposure. A top surface of the waveguides may further be polished to expose the tops of the nanopillars, revealing the internal conductors and photovoltaic material.

In an embodiment, an array of nanoscale waveguides are grown on a nonflexible substrate. For example, in an embodiment, the array of nanoscale waveguides are fabricated by sputtering a layer of titanium (Ti) film onto a nonflexible substrate. A selected thickness of catalytic transition metal (for example nickel) is electrodeposited onto the Ti film followed by carbon nanotube growth. The thickness of the Ti film may range from about 10 nm to about 100 nm or more. The CNT nanopillars may further be coated with a film of material, for example, a film of SOG. The thickness of the SOG film may be up to 100 nm or more. A film of silver (Ag) may further be deposited on the SOG coated nanopillars, forming Ag/SOG/CNT nanopillars. The thickness of the Ag film may be up to 50 nm or more. Once the Ag/SOG/CNT nanopillars have been fabricated, a photovoltaic semiconductor material (for example p-i-n amorphous Si) is deposited on the Ag/SOG/CNT nanopillars via PECVD. The thickness of the Si may be from about 10 nm to about 150 nm or more. A suitable conductor material is then deposited/evaporated on the photovoltaic coated nanopillars to complete the array of nanoscale waveguides. In an embodiment, the conductor material is indium tin oxide (ITO), which is sputter deposited. The thickness of the ITO may be up to 100 nm or more. In an embodiment, the conductor material is aluminum, which is thermally evaporated. It should be appreciated that any suitable conductor may be deposited as the presently disclosed embodiments are not intended to be limited in this manner. A flexible material, such as PDMS, may be spun-coat over a top surface of the array of nanoscale waveguides. The thickness of the PDMS film may be up to 10 micrometers or more. The film of flexible material may be soft-cured over the array of nanoscale waveguides, creating a flexible substrate. Curing may involve about 24 hours at room temperature, about 2 hours at about 60° C., or about 20 minutes at about 130° C.

FIG. 2B shows an alternate embodiment of a PV device 340 having an array of nanoscale waveguides 370. In the embodiment shown in FIG. 2B, the external electrodes 330 are local coatings that surround (coaxially) the photovoltaic material 320. As shown in FIG. 2B, the distance from the center of one carbon nanotube 310 to the center of another carbon nanotube 310, c, ranges from about 100 nanometers (nm) to about 10 micrometers (μm). In an embodiment, the distance c is about 1 μm. The distance from one nanoscale waveguide 370 to another nanoscale waveguide 370, s, ranges from about 10 nm to about 1 μm. In an embodiment, the distance s is about 100 nm.

In a PV device 360 shown in FIG. 2C, the entire array of nanoscale waveguides 370 are filled with stabilizing materials such as spin-on-glass (SOG) 380 which does not affect array functionality but stabilizes the array of nanoscale waveguides 370 and allows a top part of the nanoscale waveguides 370 to be mechanically polished off. This way nanoscale waveguide 370 cores could be exposed and work as transmission lines.

Incoming light in the form of photons is received by the internal electrodes of the nanocoaxial devices, either through the nano-antennas of the internal electrodes, or by the internal electrodes without the aid of the nano-antenna. The photon's electromagnetic energy enters each internal electrode as a subwavelength transverse electromagnetic (TEM), a subwavelength transverse magnetic (TM), or a subwavelength transverse electric (TE) mode wave. The electromagnetic wave travels primarily in the annulus between the nanoscale waveguides metal layers, i.e. in the region containing the photovoltaic material. Once the light wave enters the internal electrode, the electric field in the wave generates electron-hole pairs, known as excitons, via the photovoltaic effect, with electrons being accelerated by the internal electric field toward one metal electrode (internal or external) and holes toward the other. This photovoltaic effect thus causes each nanoscale waveguide in the array to function as an energy source, like a battery, by increasing the potential difference (voltage) between the internal and external electrodes. The voltage increase occurs as a pulse of potential energy, one for each collected quantum of incident light (photon), and subsequently each generated and dissociated exciton.

A small built-in electric field, oriented radially outward from the internal metallic electrode of the nanoscale waveguide to the external metallic layer, exists in each nanoscale waveguide due to the coaxial construction. This field is established either as a result of a natural Schottky barrier which occurs whenever a metal-semiconductor interface is formed, or as a result of intentional deposition of n-type (electron-doped) and p-type (hole-doped) doping layers on either side of the central intrinsic semiconductor PV material. Alternatively, the intrinsic layer is not employed, and instead only an n-type followed by a p-type layer fills the annulus.

The internal electrode nanopillar may be a metallic core. Examples of metals for the internal electrode include, but are not limited to, carbon fiber; carbon nanotube; pure transition metals such as nickel (Ni), aluminum (Al), or chromium (Cr); metal alloys, e.g. stainless steel (Fe/C/Cr/Ni) or aluminum alloys (Al/Mn/Zn); and metallic polymers. Other internal electrodes are highly doped semiconductors, and semi-metals (metals with vanishingly small band gap, e.g. graphite). In an embodiment, the internal electrode is a carbon nanotube. Those skilled in the art will recognize that the internal electrode may be other conducting materials known in the art and be within the spirit and scope of the presently disclosed embodiments. The internal electrode has a diameter ranging from about 1 nanometer (nm) to about 600 nanometers.

In an embodiment, the photovoltaic material is chosen such that the material has a band gap to maximize the absorption of light in the visible spectrum. Examples of photovoltaic materials include, but are not limited to, silicon (Si), cadmium telluride (CdTe), indium gallium phosphide (InGaP), gallium arsenide (GaAs), germanium (Ge), Cu(InGa)Se, GaP, CdS, indium antimonide (InSb), lead telluride (PbTe), $In_{1-x}Ga_xN$, organic semiconductors (e.g., copper phthalocyanine (CuPc)), dielectric materials, and similar materials known to those skilled in the art. The photovoltaic material may possess a band gap comparable to the action potential of ganglion cells or horizontal cells in the retina. The photovoltaic materials may be crystalline (periodic arrangement of atoms in macroscopic scale), polycrystalline (periodic arrangement of atoms in microscopic scale), or amorphous (aperiodic arrangement of atoms in macroscopic scale). Those skilled in the art will recognize that the photovoltaic material may be other materials known in the art having a band gap so as to improve the absorption of light in the visible spectrum. The photovoltaic material may be uniform around the internal electrode or the photovoltaic material may surround the internal electrode in a non-uniform manner. The thickness of the photovoltaic material should be approximately the same as or less than the carrier diffusion length. For example, in amorphous silicon (Si), the carrier diffusion length is about 100 nm. The photovoltaic material has a thickness ranging from about 1 nanometer (nm) to about 600 nanometers. For TEM propagation, the overall inter-electrode spacing in the waveguide should be approximately the same as the photovoltaic material.

In an embodiment, the photovoltaic material has a band gap that extends over a wide energy range, thus providing a match to a broad spectrum of electromagnetic radiation. In an embodiment, the photovoltaic material has a band gap corresponding to the visible spectrum. In an embodiment, the photovoltaic material has a band gap corresponding to the UV spectrum. In an embodiment, the photovoltaic material has a band gap corresponding to the infrared spectrum.

The external electrode may be a metal. Thus, the external electrode may take the form of a metallic cylinder. Examples of external electrodes include but are not limited to, carbon fiber; carbon nanotube; pure transition metals such as nickel (Ni), aluminum (Al), or chromium (Cr); metal alloys e.g. stainless steel (Fe/C/Cr/Ni) or aluminum alloys (Al/Mn/Zn); and metallic polymers. Other external electrodes are highly doped semiconductors, and semi-metals (metals with a vanishingly small band gap, e.g. graphite). Those skilled in the art will recognize that the external electrode may be other conducting materials known in the art and be within the spirit and scope of the presently disclosed embodiments. The external electrode has a diameter ranging from about 10 nanometer (nm) to about 1000 nanometers.

Carbon nanotube tubule diameter, tubule length, number of concentric graphene layers (graphitization) comprising individual tubules, site density, and the yield of the carbon nanotubes may be controlled by varying the reaction temperature of a carbon nanotube synthetic process. In an embodiment, the site density of carbon nanotubes is controlled to mimic the site density of photoreceptors in the human retina.

In an embodiment, carbon nanotubes are obtained by placing a catalyst substrate material, which is formed by electrochemical deposition of catalytic transition metal microparticles, with a pre-determined site density, on a metal coated non-metallic substrate material, within a PECVD chamber known in the art, following which carbon nanotube growth is initiated on the surface of the catalyst substrate material by standard methods described in the art. (see for example Z. F. Ren, et al., Science, 282, 1105 (1998); Z. P. Huang, et al., Appl. Phys. A: Mater. Sci. Process, 74, 387 (2002); and Z. F. Ren et al., Appl. Phys. Lett., 75, 1086 (1999), the contents of which are incorporated herein by reference in their entirety).

Production of linear carbon nanotubes may be accomplished by placing a catalyst substrate material into the reaction chamber of a CVD apparatus and exposing the substrate to a flow of carbon gas alone or in combination with a promoter gas. The reaction temperature, gas pressure, and reaction time are maintained under pre-determined conditions effective to cause formation and growth of a plurality of carbon nanotubes on the catalyst substrate surface. The CVD chamber temperature and gas pressure are optimized to control and obtain the desired morphology of carbon nanotubes during growth.

The morphology of the carbon nanotubes is related to the size of the catalytic transition metal microparticles deposited on the metal coated non-metallic substrate. When the diameter of the catalytic transition metal microparticles is smaller than 50 nanometers, either no carbon nanotubes or only short and curved carbon nanotubes are grown. When the size of the catalytic transition metal microparticles is large, well-aligned carbon nanotubes with uniform length distribution are grown. In an embodiment, the catalyst substrate is optionally etched by applying low intensity plasma to the substrate for a short time before the introduction of acetylene gas to substantially reduce the number of catalytic transition metal microparticles that have a diameter smaller than 50 nanometers. In an embodiment, the catalyst substrate is etched by applying 100 Watts of direct current (DC) plasma is for about 10 to about 20 seconds.

In an embodiment, a nanoscale PV device of the presently disclosed embodiments is fabricated to yield a visual neuroprosthesis that can be placed in a retina. The visual neuroprosthesis comprises an array of nanoscale waveguides that are able to receive, propagate, and convert incident visible light into electrical neural signals. The visual neuroprosthesis is biocompatible and communicates with cells of the retina. The cells of the retina then transfer the converted electrical neural signals to optic nerve fibers where they travel to the brain and are turned into visual images. The nanoscale waveguides in the visual neuroprosthesis have a photovoltaic (PV) material located between an internal metallic electrode and an external metallic electrode. The internal electrode acts as an optical antenna with an impedance-matched transmission line. In the embodiments depicted herein, the internal metallic electrode is a carbon nanotube. Those skilled in the art will recognize that the material comprising the internal electrode need not be carbon and still be within the scope and spirit of the presently disclosed embodiments.

The site density of carbon nanotubes in the visual neuroprosthetic device of the presently disclosed embodiments may be precisely controlled. For example, the visual neuroprosthetic device may have a high site density, a low site density, or a combination of a high and low site density. In an embodiment, the site density varies within the visual neuroprosthetic device such that a high site density exists at one area of the device and a low site density at another area of the device. The precise control of the site density allows for a visual neuroprosthetic device that mimics the density of photoreceptors of the human retina. The site density of carbon nanotubes within a visual neuroprosthetic device may be controlled on an individual basis.

Figure 3A:
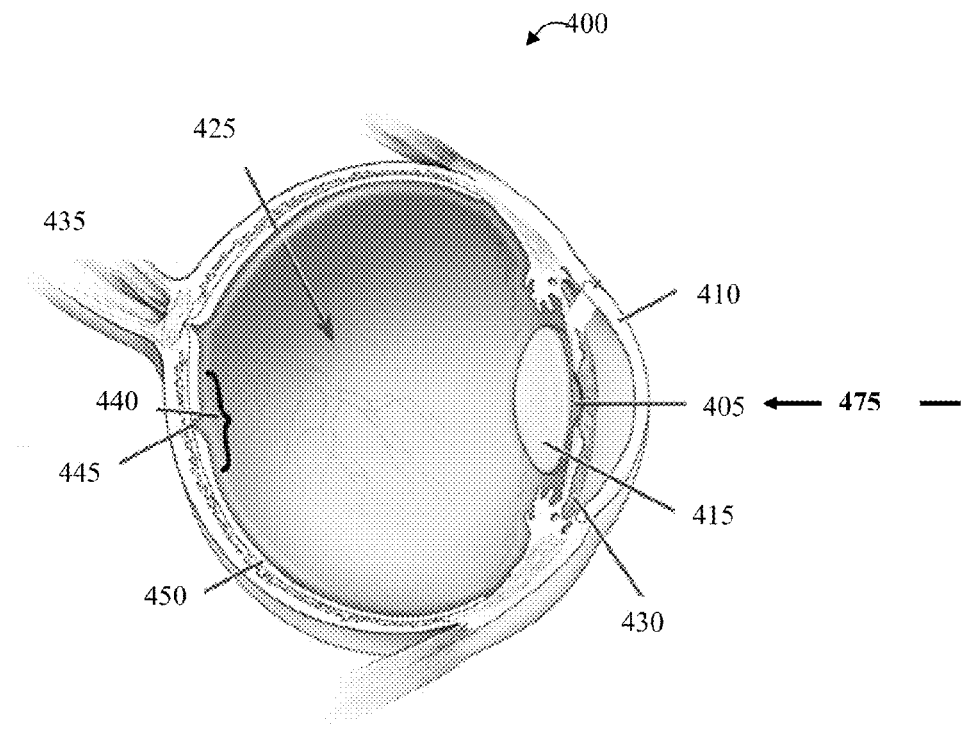
FIG. 3A and FIG. 3B show parts of a human eye.

FIG. 3A shows a schematic view of a human eye 400. The eye 400 is typically roughly spherical, filled with a transparent gel-like substance called a vitreous body 425. Light 475 (arrow) enters a pupil 405, is focused and inverted by a cornea 410 and a lens 415, and is projected onto a light-sensitive panel of cells known as a retina 450 at the rear of the eye 400, where the light 475 is detected and converted into electrical neural signals. An area of the retina 450 that lacks light-sensitive cells is known as "the blind spot". This area appears as an oval white area of about 3 mm$^2$. Temporal to this area is a macula 440. At the center of the macula 440 is a fovea 445, a 0.3 mm diameter area that is most sensitive to light 475 and is responsible for sharp central vision. The output of the retina 450 is channeled through a layer of retinal ganglion cells whose axons form an optic nerve 435 connecting the eye 400 and brain. The actual light-sensitive cells (or photoreceptors) are know as rods and cones, but the ganglion cells transmit the electrical signals to the brain.

Figure 3B:
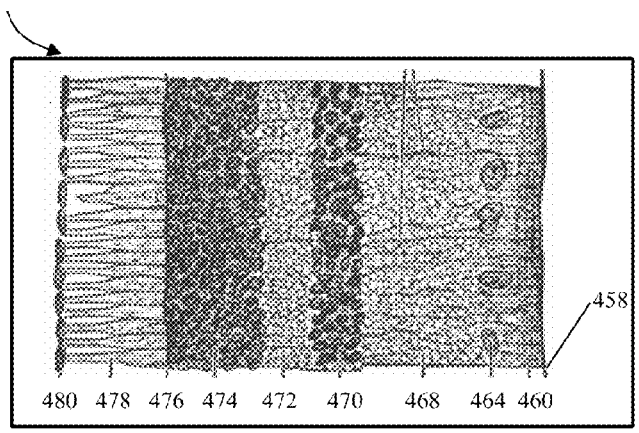

FIG. 3B shows a cross-sectional view of the ten distinct layers of the retina 450. These distinct layers of alternating cells and processes convert a light signal into a neural signal ("signal transduction"). From innermost to outermost, the ten distinct layers of cells and processes include: an inner limiting membrane 458, which is the boundary between the retina 450 and the vitreous body 425; a nerve fiber layer 460 which is formed by the expansion of fibers of the optic nerve; a ganglion cell layer 464 which consists of a layer of ganglion cells; an inner plexiform layer 468 which is made up of a dense reticulum of minute fibrils formed by the interlacement of dendrites of the ganglion cells with those of the cells of the next layer; an inner nuclear layer 470 which is made up of a number of closely packed intermediate cells: the bipolar cells, the horizontal cells, and the amacrine cells; an outer plexiform layer 472 which is a layer that consists of a dense network of synapses between dendrites of the horizontal cells from the inner nuclear layer 470, and photoreceptor cell inner segments from the next layer; an outer nuclear layer 474 which like the inner nuclear layer 470, contains several strata of oval nuclear bodies: rod and cone granules; an external limiting membrane 476 which is a layer that separates the inner segment portions of the photoreceptors from their cell nuclei; a photoreceptor layer 478 which comprise the rods and cones; and a retinal pigment epithelium layer 480 which is the pigmented cell layer just outside the neurosensory retina 450 that nourishes retinal visual cells, and is firmly attached to the underlying choroid and overlying retinal visual cells.

In a normal functioning retina, light enters from the ganglion cell layer 464 side first, and must penetrate all cell types before reaching the rods and cones of the photoreceptor layer 478. The outer segments of the rods and cones transduce the light and send the signal through the cell bodies of the outer nuclear layer 474 and out to their axons.

The retina contains two types of photoreceptors, rods and cones. The mechanism by which light energy is converted to neuronal signals is exactly the same in both rods and cones; the difference between the two types of receptors are in the visual pigments involved. The rods are most sensitive to light and dark changes, shape and movement and contain only one type of light-sensitive pigment. The rods are more numerous, some 120 million, and are more sensitive than the cones however, they are not sensitive to color. The 6 to 7 million cones are not as sensitive to light as the rods but are most sensitive to one of three different colors (green, red or blue). Signals from the cones are sent to the brain which then translates these messages into the perception of color.

Figure 4:
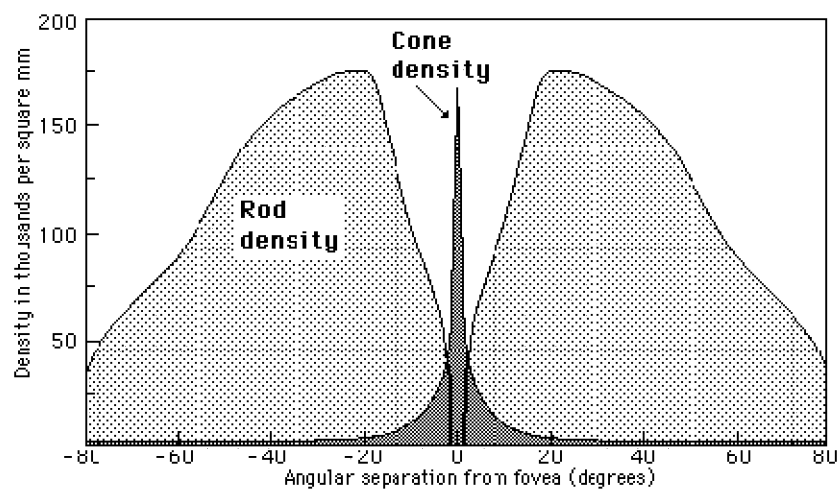
FIG. 4 shows measured density curves for rods and cones of the human retina.

The density of the rods and cones vary in the retina. As shown in the graph of FIG. 4, cones are concentrated in the fovea, and the rods are absent there but present at high density throughout most of the retina. The fovea contains the highest density of cone photoreceptors in the retina, an average of about $162,000/mm^2$. The highest rod densities are located about 3 mm to about 5 mm from the center of the fovea in an elliptical ring around the fovea at about $176,000/mm^2$.

Figure 5:
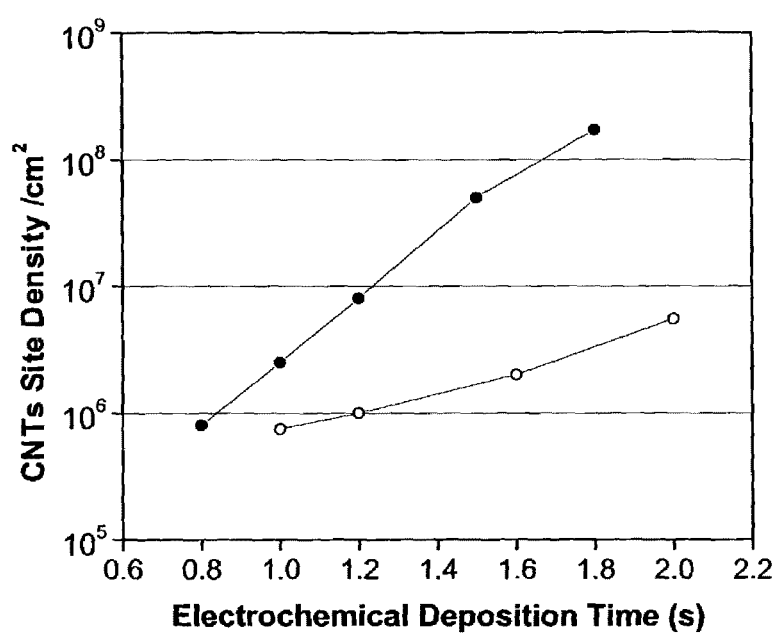
FIG. 5 shows carbon nanotube site density dependence of electrochemical deposition current density on deposition time at a current density of 1.0 mA/cm² (open circles) and 2.0 mA/cm² (filled circles).

The ability to control the site density of nanoscale waveguides in the visual neuroprosthetic device of the presently disclosed embodiments allows for devices that can closely mimic the human retina, a huge improvement over prior visual neuroprosthetic devices where not enough electrodes are possible for visual acuity. The visual neuroprosthetic devices of the presently disclosed embodiments may provide site densities of nanoscale waveguides up to about $10^6/mm^2$, which is larger than the site density of rods and cones in the human retina. FIG. 5 shows that by adjusting the current density and the deposition time, aligned carbon nanotubes with site densities ranging from about $1\times10^5/cm^2$ ($1\times10^3/mm^2$) to about $1\times10^8/cm^2$ ($1\times10^6/mm^2$) are achievable. For example, at a current density of about $1.0$ mA/$cm^2$, the carbon nanotube site density increases to about 8 times when the deposition time increases from about 1.0 to about 2.0 seconds, whereas at a deposition time of about 2.0 mA/$cm^2$, the carbon nanotube site density increased greater than about 100 times when the deposition time increases from about 0.8 to about 1.8 seconds. Moreover, using conventional lithographic techniques, nanopillar/nanocoax site density may be accurately varied across a substrate.

Figure 6A:
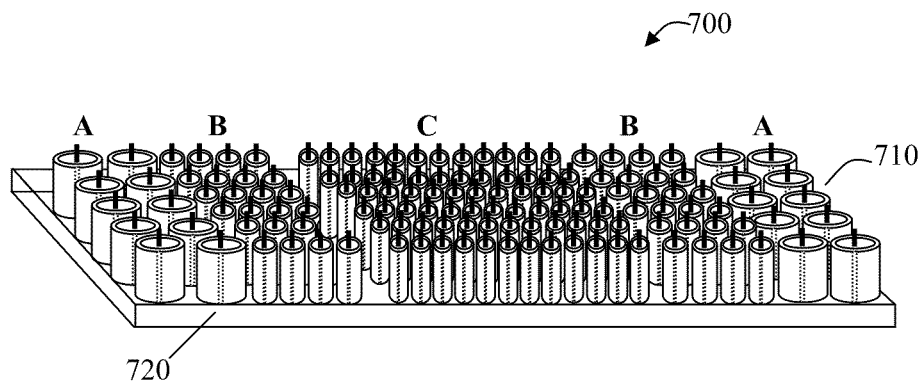
FIG. 6A, FIG. 6B, and FIG. 6C show schematic representations of visual prosthetic devices of the presently disclosed embodiments.
Figure 6B:
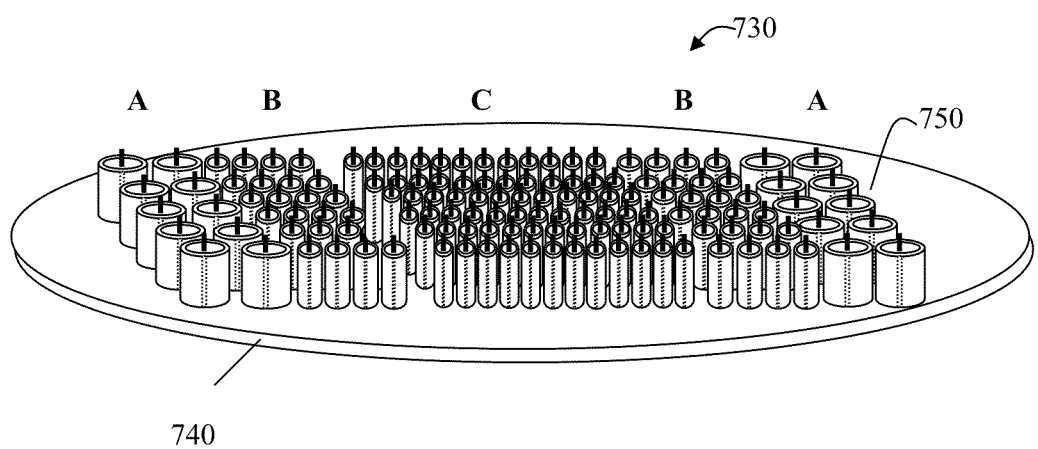
Figure 6C:
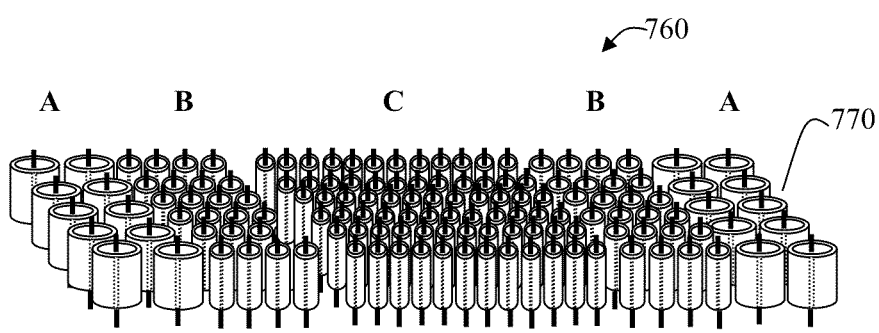

FIG. 6A, FIG. 6B and FIG. 6C show schematic views of visual neuroprosthetic devices of the presently disclosed embodiments. The devices have a thickness that is defined by the length of the nanoscale waveguides and range from about 1 μm to about 10 μm. In the embodiment depicted in FIG. 6A, a visual neuroprosthetic device 700 includes a transparent substrate 720 supporting an array of nanoscale waveguides 710. The substrate 720 is rectangular in shape. In the embodiment depicted in FIG. 6B, a visual neuroprosthetic device 730 includes a transparent substrate 740 supporting an array of nanoscale waveguides 750. The substrate 740 is circular in shape. Those skilled in the art will recognize that the substrates may be any shape and be within the scope and spirit of the presently disclosed embodiments. In the embodiment depicted in FIG. 6C, a visual neuroprosthetic device 760 includes an array of nanoscale waveguides 770 that are not supported by any substrate. The devices may comprise a mechanically stabilizing layer of spin-on-glass (SOG) or another similar material that is biocompatible within the human eye. The substrates of FIGS. 6A and 6B can be flexible or rigid. The substrates of FIGS. 6A and 6B can be transparent or nontransparent.

The site density of nanoscale waveguides can vary throughout the devices, as well as the diameter of the nanoscale waveguides. In an embodiment, the site density of nanoscale waveguides varies to closely resemble the density of photoreceptors found in the human retina. In an embodiment, the site density of nanoscale waveguides varies to closely resemble the density of photoreceptors found in the macula. In an embodiment, the site density of nanoscale waveguides varies to closely resemble the density of photoreceptors found in the human elliptical ring around the fovea. For example, for the visual neuroprosthetic devices shown in FIG. 6A, FIG. 6B, and FIG. 6C, the density of nanoscale waveguides is matched to the elliptical ring around the fovea. As can be seen, sections "A" have a smaller density than sections "B". Section C has the highest density of nanoscale waveguides, similar to the higher number of photoreceptors that are present in the fovea and elliptical ring around the fovea.

In an embodiment, the diameter of nanoscale waveguides varies to closely resemble the diameter of photoreceptors found in the human elliptical ring around the fovea. For example, for the visual neuroprosthetic devices shown in FIG. 6A, FIG. 6B, and FIG. 6C, the diameter of nanoscale waveguides varies. As can be seen, the nanoscale waveguides of sections "A" have a larger diameter than those in sections "B". Section C has nanoscale waveguides with the smallest diameter. The variations in the diameter of nanoscale waveguides in the visual neuroprosthetic devices of the presently disclosed embodiments may lead to differentiation of performance, tunable to mimic both the rods and cons found in the eye. Those skilled in the art will recognize that the number of nanoscale waveguides, the site density of nanoscale waveguides, and the lengths and diameters of tubules may vary and still be within the scope and spirit of the presently disclosed embodiments.

In the embodiment depicted in FIG. 6A and FIG. 6B, an optical nano-antenna protrudes from a surface of each nanoscale waveguide. In the embodiment depicted in FIG. 6C, an optical nano-antenna protrudes from both a top surface and a bottom surface of each nanoscale waveguide. It should be noted that not all embodiments are limited to optical nano-antennas that protrude out from a surface of the visual neuroprosthetic devices. For example, in an embodiment, a visual neuroprosthetic device has optical nano-antenna's that do not protrude from a surface. Each nanoscale waveguide in the array is capable of receiving and transmitting an electromagnetic radiation. The incoming light, is compressed into nanoscopic channels of the transmission lines of the internal electrode, and is subsequently decompressed (and reemitted) on the opposite side of the device.

The coaxial nanoscale waveguides of the presently disclosed embodiments do not have a cut-off frequency (in contrast to waveguides), i.e. the nanoscale coaxial configuration allows for propagation of radiation with wavelength exceeding their perpendicular dimensions. The external radiation is channeled and compressed into the confined space between the internal and external electrodes.

Figure 7:
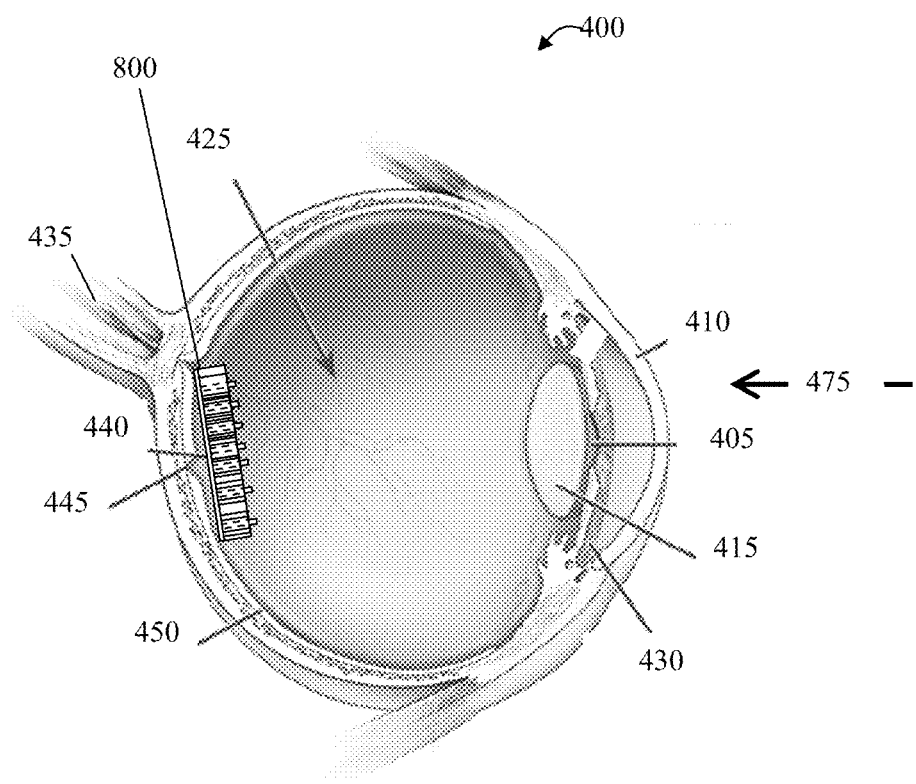
FIG. 7 shows the placement of a visual prosthetic device of the presently disclosed embodiments within the human eye.

FIG. 7 shows a visual neuroprosthetic device 800 of the presently disclosed embodiments in place within a human eye 400. In the embodiment depicted in FIG. 7, the device 800 has been placed in the elliptical ring around the fovea 445. The elliptical ring is a circular field of approximately 6 mm around the fovea and is considered the central retina while beyond this is peripheral retina. The device 800 may be fabricated to have dimensions which resemble the dimensions of the central retina, about a 6 mm device. In an embodiment, the device 800 conforms to the curvature of the back of the eye. Those skilled in the art will recognize that the size, shape and dimensions of the device 800 may be varied and still be within the scope and spirit of the presently disclosed embodiments. The array of nanoscale waveguides engage and communicate with the layers of the retina 450. The cell processes of the retina 450 may intertwine with and migrate to the nanoscale waveguides of the device 800 so that the device 800 becomes part of the retinal layers. Each captured photon generates a voltage pulse and/or a current pulse, which is sensed by one or more cells in the retina. These may be one or more of the bipolar, amacrine or ganglion cells and axons, or other cells in the optic nerve pathway, such as those in the inner plexiform layer.

Retinal prostheses are divided into two subcategories depending on where the stimulating electrodes are placed. In the epiretinal approach, the electrodes are located on the inner limiting membrane between the retina and the vitreous body to produce phosphenes. In the subretinal approach, the electrodes are located in place of the photoreceptors and used to generate currents, which stimulate the retina. The devices of the presently disclosed embodiments may be used in both the epiretinal approach and the subretinal approach, as well as other areas of the eye as long as the nanoscale waveguides are in communication with the cells of the retina and are able to transfer electrical neural signals to the cells.

Figure 8:
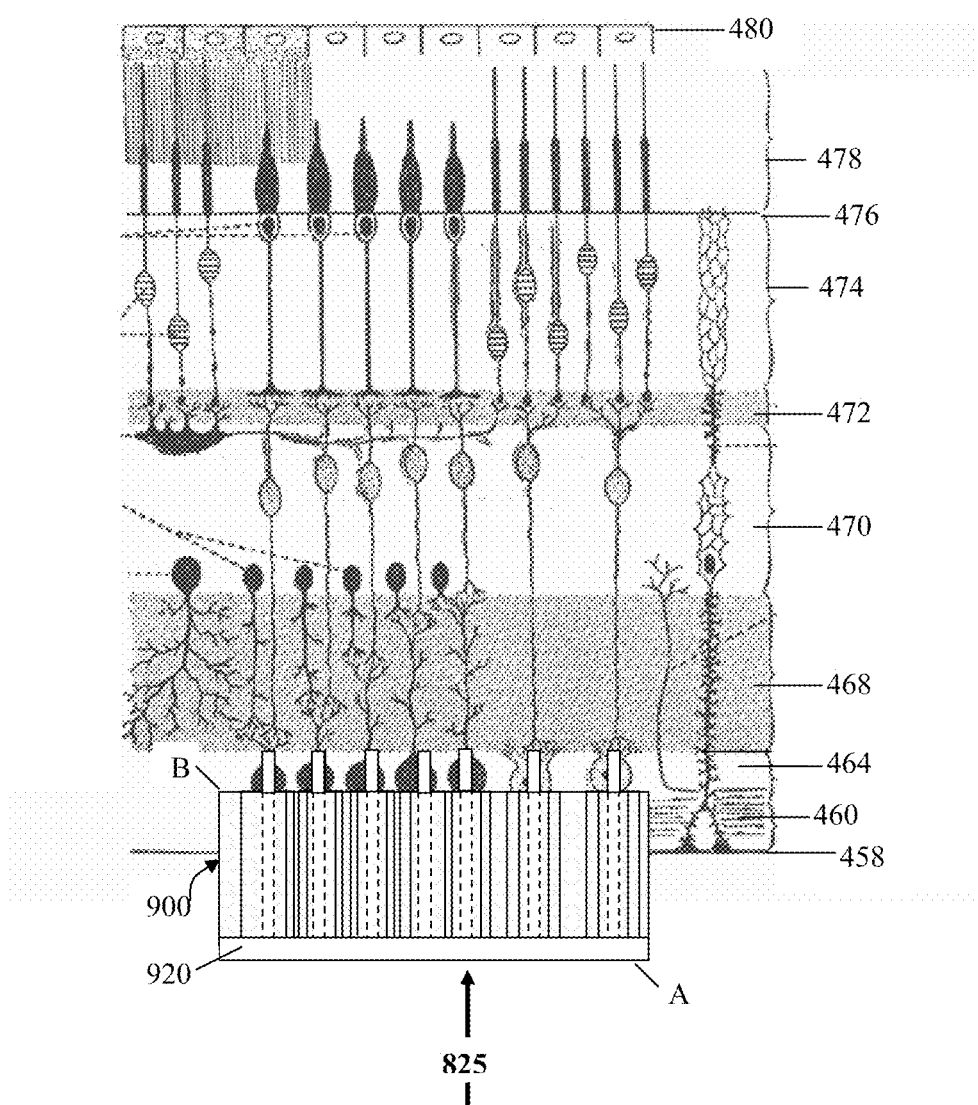
FIG. 8 shows a schematic illustration of a visual prosthetic device of the presently disclosed embodiments in an epiretinal space of the retina.

FIG. 8 shows a close-up diagram of the relationship between the layers and processes of the retina and a visual neuroprosthetic device 900. The visual neuroprosthetic device 900 comprises an array of coaxial nanoscale waveguides that are supported by a transparent substrate 920 and surrounded with a biocompatible mechanical stabilizing film. In the embodiment depicted in FIG. 8, nano-antennas of internal electrodes of the nanoscale waveguides protrude from a back surface "B" of the device. In an embodiment, nano-antennas do not protrude out from the back surface of the device. FIG. 8 shows the device 900 in the epiretinal space of the eye in front of the internal limiting membrane 458. The device 900 may be placed in another layer and still be within the scope and spirit of the presently disclosed embodiments, as long as the nanoscale waveguides are engaged with the cells of the retina and are able to communicate with processes of the cells such that converted electrical neural signals produced by the nanoscale waveguides are able to be transferred to the cells and transferred to optic nerve fibers where they travel to the brain and are turned into visual images.

In FIG. 8, incoming light 825 (arrow) passes through the transparent substrate 920 and received by the nanoscale waveguides. The light 825 propagates through the nanoscale waveguides, where it is converted into electrical neural signals via the photovoltaic effect. The converted electrical neural signals are presented to the nano-antennas on surface "B" of the device where they are sensed by ganglion cells within the inner plexiform layer 468. The converted electrical neural signals move through the ganglion cells whose axons form the fiber of the optic nerve in the nerve fiber layer 460. The signals move through the optic nerve fibers and are sent to the brain to be interpreted.

Figure 9:
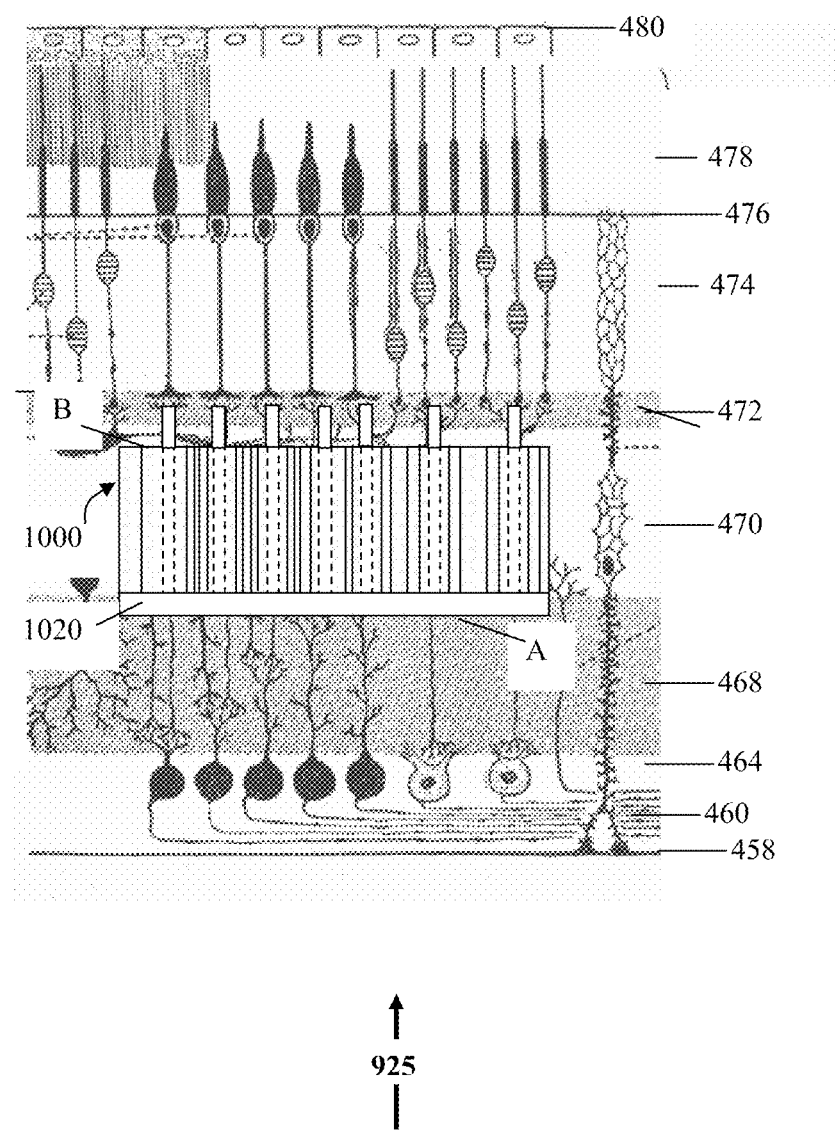
FIG. 9 shows a schematic illustration of a visual prosthetic device of the presently disclosed embodiments in an epiretinal space of the retina.

FIG. 9 shows a close-up diagram of the relationship between the layers and processes of the retina and a visual neuroprosthetic device 1000. The visual neuroprosthetic device 1000 comprises an array of coaxial nanoscale waveguides that are supported by a transparent substrate 1020 and surrounded with a biocompatible mechanical stabilizing film. In the embodiment depicted in FIG. 9, nano-antennas of internal electrodes of the nanoscale waveguides protrude from a back surface "B" of the device. In an embodiment, nano-antennas do not protrude out from the back surface of the device. FIG. 9 shows the visual prosthetic device 1000 in another area of the epiretinal space of the eye. The nano-antennas that protrude out of the visual prosthetic device 1000 are engaged with the cells of the retina and are able to communicate with processes of the cells such that converted electrical neural signals produced by the nanoscale waveguides are able to be transferred to the cells and transferred to optic nerve fibers where they travel to the brain and are turned into visual images.

In FIG. 9, incoming light 925 (arrow) passes through the transparent substrate 1020 and received by the nanoscale waveguides. The light 925 propagates through the nanoscale waveguides, where it is converted into electrical neural signals via the photovoltaic effect. The converted electrical neural signals are presented to the nano-antennas on surface "B" of the device where they are transferred to intermediate cells within the inner nuclear layer 470. The converted electrical neural signals then travel through the intermediate cells of the inner nuclear layer 470, through the inner plexiform layer 468 and synapse with dendrites of ganglion cells of the ganglion cell layer 464. The converted electrical neural signals move through the ganglion cells whose axons form fiber of the optic nerve in the nerve fiber layer 460. The signals move through the optic nerve fibers and sent to the brain to be interpreted.

Figure 10:
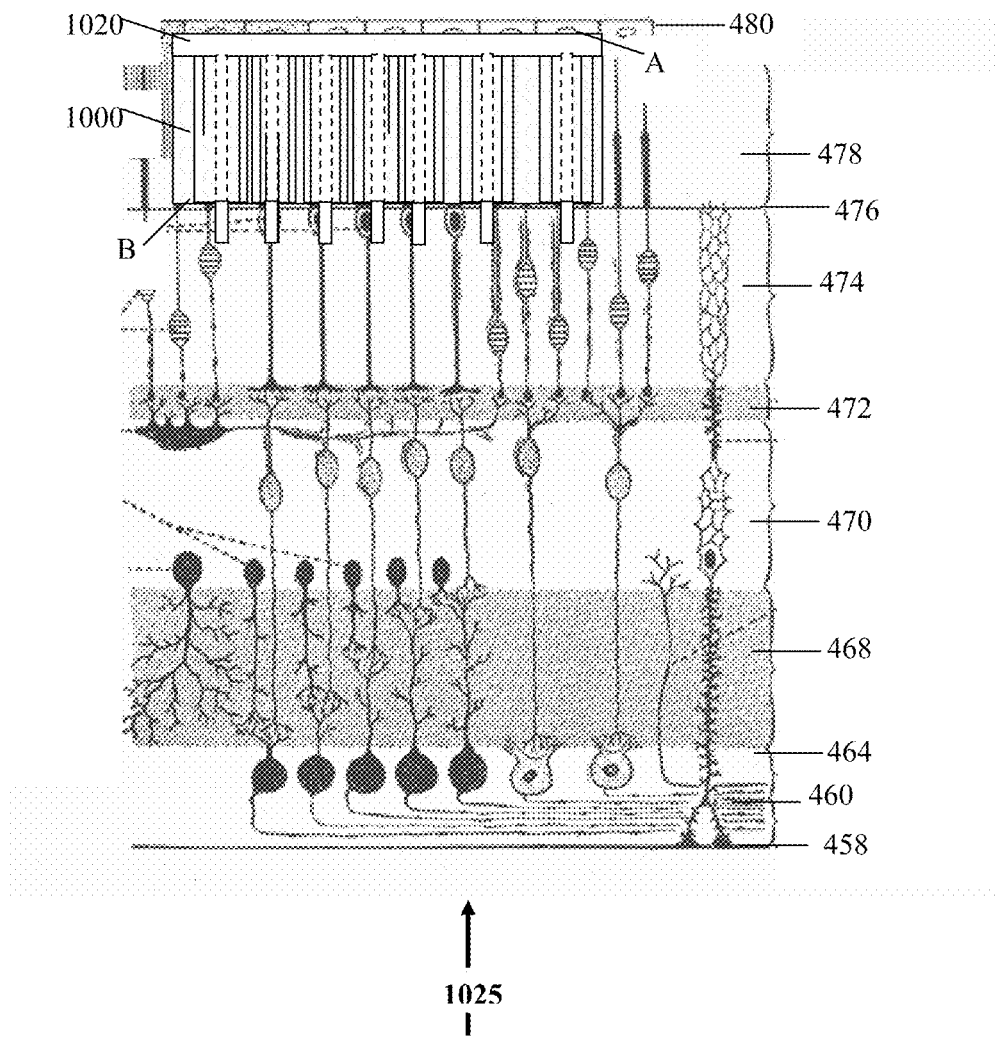
FIG. 10 shows a schematic illustration of a visual prosthetic device of the presently disclosed embodiments in a subretinal space of the retina.

FIG. 10 shows a close-up diagram of the relationship between the layers and processes of the retina and a visual neuroprosthetic device 1000. The visual neuroprosthetic device 1000 comprises an array of coaxial nanoscale waveguides that are supported by a substrate 1020 and surrounded with a biocompatible mechanical stabilizing film. The substrate 1020 is preferably nontransparent. In the embodiment depicted in FIG. 10, nano-antennas of internal electrodes of the nanoscale waveguides protrude from a back surface "B" of the device. In an embodiment, nano-antennas do not protrude out from the back surface of the device. FIG. 10 shows the visual prosthetic device 1000 in the subretinal space of the retina, where the array of nanoscale waveguides take the place of damaged photoreceptors. The nano-antennas that protrude out of the visual prosthetic device 1000 are engaged with the cells of the retina and are able to communicate with processes of the cells such that converted electrical neural signals produced by the nanoscale waveguides are able to be transferred to the cells and transferred to optic nerve fibers where they travel to the brain and are turned into visual images.

In FIG. 10, incoming light 1025 (arrow) is received by the nanoscale waveguides. Nano-antennas at surface "B" of the device capture the incoming light 1025 and propagate the light through the nanoscale waveguides, where it is converted into electrical neural signals via the photovoltaic effect. The converted electrical neural signals are presented to the nano-antennas on surface "B" of the device where they are transferred to intermediate cells within the inner nuclear layer 470. The converted electrical neural signals then travel through the intermediate cells of the inner nuclear layer 470, through the inner plexiform layer 468 and synapse with dendrites of ganglion cells of the ganglion cell layer 464. The converted electrical neural signals move through the ganglion cells whose axons form fiber of the optic nerve in the nerve fiber layer 460. The signals move through the optic nerve fibers and sent to the brain to be interpreted.

In an embodiment, a PV device of the present disclosure is fabricated by growing an array of nanoscale waveguides on a nonflexible substrate. For example, in an embodiment, the array of nanoscale waveguides are fabricated by sputtering a layer of titanium (Ti) film onto a nonflexible substrate. A selected thickness of catalytic transition metal (for example nickel) is electrodeposited onto the Ti film followed by carbon nanotube growth. The thickness of the Ti film may range from about 10 nm to about 100 nm or more. The CNT nanopillars may further be coated with a film of material, for example, a film of SOG. The thickness of the SOG film may be up to 100 nm or more. A film of silver (Ag) may further be deposited on the SOG coated nanopillars, forming Ag/SOG/CNT nanopillars. The thickness of the Ag film may be up to 50 nm or more. Once the Ag/SOG/CNT nanopillars have been fabricated, a photovoltaic semiconductor material (for example p-i-n amorphous Si) is deposited on the Ag/SOG/CNT nanopillars via PECVD. The thickness of the Si may be from about 10 nm to about 150 nm or more. A suitable conductor material is then deposited/evaporated on the photovoltaic coated nanopillars to complete the array of nanoscale waveguides. In an embodiment, the conductor material is indium tin oxide (ITO), which is sputter deposited. The thickness of the ITO may be up to 100 nm or more. In an embodiment, the conductor material is aluminum, which is thermally evaporated. It should be appreciated that any suitable conductor may be deposited as the presently disclosed embodiments are not intended to be limited in this manner. A flexible material, such as PDMS, may be spun-coat over a top surface of the array of nanoscale waveguides. The thickness of the PDMS film may be up to 10 micrometers or more. The film of flexible material may be soft-cured over the array of nanoscale waveguides, creating a flexible substrate. Curing may involve about 24 hours at room temperature, about 2 hours at about 60° C., or about 20 minutes at about 130° C.

In an embodiment, the nonflexible substrate is separated from the array of nanoscale waveguides having the flexible substrate. Separation can involve breaching an interface between any of the various layers making up the PV device of the present disclosure. In an embodiment, in order to remove the nonflexible substrate from the array/flexible substrate, the PV device is thermally cycled in liquid nitrogen to induce separation and break the bonds between the various layers (e.g., via delamination). In an embodiment, the liquid nitrogen treatment may be followed or replaced by a hot plate thermal cycle. In an embodiment, the PV device may be heated for about 2 minutes at a temperature between about 80° and about 100° C. or more. In an embodiment, the thermal treatment may further include repeating the liquid nitrogen and/or hot plate thermal procedures more than one time. In an embodiment, the thermal treatment breaks the bonds between the various layers of the PV device based on the principle of differential thermal expansion, since the thermal expansion coefficients are different among the constituent coating materials. In an embodiment, the thermal treatment results in separation of the coaxial nanoscale waveguides and flexible substrate from the nonflexible substrate, resulting in a flexible array. In an embodiment, separation may occur between the SOG and Ti films.

After thermal treatment, coatings on the film may be removed to expose layers of coaxial nanoscale waveguides. Coatings may be removed by removing SOG, removing Ag, and removing ITO. In an embodiment, removal of SOG may include methods known in the art, such as about 2.5 M KOH for about 2 min. In an embodiment, removal of Ag may include methods known in the art, such as Ag etchant. In an embodiment, removal of ITO may include methods known in the art, such as diluted HCl at about 25° C. Removal of SOG, Ag and ITO may occur through other methods known in the art as the presently disclosed embodiments are not intended to be limited in this manner.

Once removed from the nonflexible substrate, the flexible array may be shaped in a variety of ways. In an embodiment, the flexible array may be shaped in such a way as to match the curvature of a natural retina, similar to that of a contact lens. Shaping of the flexible array may involve slicing or removing wedges of the flexible array. Shaping of the flexible array may occur through other methods known in the art as the presently disclosed embodiments are not intended to be limited in this manner.

Figure 11:
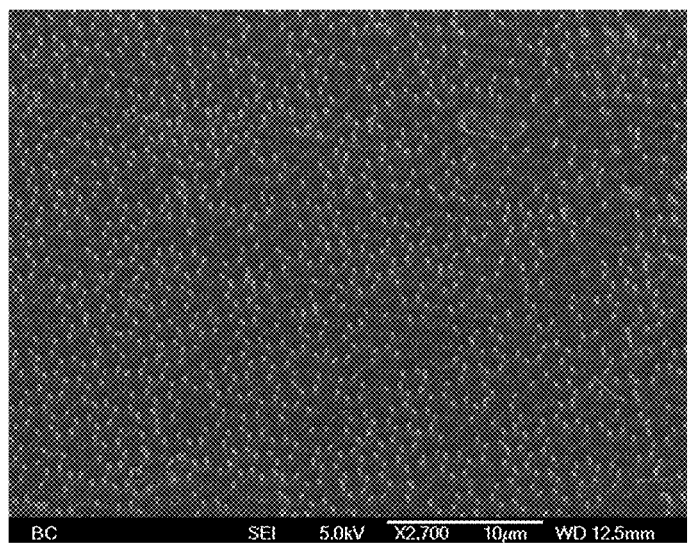
FIG. 11 shows an exemplary scanning electron microscope image of an array of exposed coaxial nanoscale waveguides on a flexible substrate after removal from a nonflexible substrate.
Figure 12:
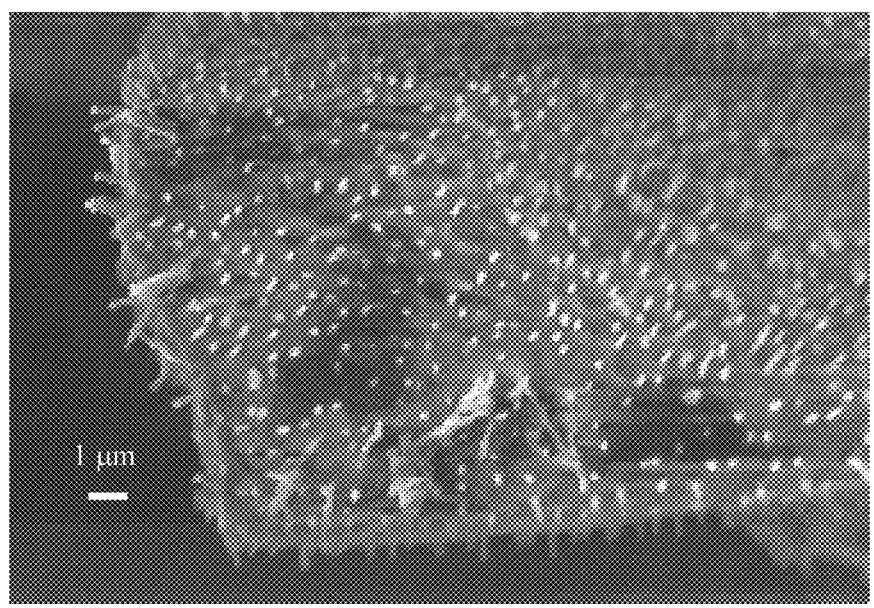
FIG. 12 shows an exemplary scanning electron microscope image of an array of exposed coaxial nanoscale waveguides on a flexible substrate after removal from a nonflexible substrate.

FIG. 11 and FIG. 12 shows an illustrative embodiment of a flexible array of the present disclosure, resulting from the separation of nonflexible substrate from the array of nanoscale waveguides having the flexible substrate. FIG. 11 shows an electron microscope image of an array of exposed coaxial nanoscale waveguides embedded in the flexible substrate, scale is 10 micrometers. FIG. 12 shows an electron microscope image of an array of exposed coaxial nanoscale waveguides on a free-standing, flexible substrate after removal from a nonflexible substrate, scale is 1 micrometers.

A visual neuroprosthetic device of the presently disclosed embodiments may be fabricated using the methods outlined below or similar methods. In an embodiment, a method for fabricating a visual neuroprosthetic device includes: sputtering a layer of chromium onto a glass substrate, typically at a thickness of about 15 nm. A selected thickness of catalytic transition metal (for example nickel) is electrodeposited onto the chromium glass followed by carbon nanotube growth. Plasma enhanced chemical vapor deposition (PECVD) is used to etch the chromium layer. Typical PECVD lasts about an hour. A photovoltaic semiconductor material (for example Si) is sputtered on the substrate. Aluminum is then sputtered (acting as an external electrode) followed by spin-coating of polymethylmethacrylate (PMMA) and baking at about 180° C. for about 40 min. Typically, about 400 nm of aluminum is sputtered. Electrochemical etching of the aluminum layer on the tips of the nanotubes is accomplished at about 25 min in about 20% $H_2SO_4$, 4.0V, sample as anode, a platinum electrode as cathode.

In an embodiment, a method for fabricating a visual neuroprosthetic device includes: sputtering a layer of chromium onto a glass substrate, typically at a thickness of about 15 nm. A selected thickness of catalytic transition metal (for example nickel) is electrodeposited onto the chromium glass followed by carbon nanotube growth. Plasma enhanced chemical vapor deposition (PECVD) is used to etch the chromium layer. Typical PECVD lasts about an hour. A photovoltaic semiconductor material (for example Si) is sputtered on the substrate. Aluminum is then sputtered onto the coated substrate. The tips of the nanotubes are removed by polishing. Electrochemical etching of the aluminum layer on the tips of the nanotubes is accomplished at about 25 min in about 20% $H_2SO_4$, 4.0V, sample as anode, a platinum electrode as cathode.

The internal electrodes, the external electrodes and the visual neuroprosthetic device may have various shapes, including but not limited to round, square, rectangular, circular, cylindrical and other symmetrical and non-symmetrical shapes. Certain shapes may be more efficient by allowing for an increase or decrease in the density of the devices on an array. Those skilled in the art will recognize that the internal electrodes, the external electrodes and the visual prosthetic device v have any shape and any cross section and still be within the spirit and scope of the presently disclosed embodiments.

The thickness of the photovoltaic material is the separation distance between the internal electrode and the external electrode. In an embodiment, the separation distance between the internal electrode and the external electrode is nanoscale and the thickness of the photovoltaic material is nanoscale. Charge carriers (electrons and holes) liberated by incident light via a photovoltaic effect need travel only nanoscale distances to be harvested in the form of electric current or voltage. The thickness of the photovoltaic material should be approximately the same as or less than the carrier diffusion length. For example, in amorphous silicon (Si), the carrier diffusion length is about 100 nm. For TEM propagation, the overall inter-electrode spacing in the cometal structure should be approximately the same as the photovoltaic material.

For a sufficiently large inter-electrode spacing, multi-mode propagation occurs in which the TE (transverse electric) and/or TM (transverse magnetic) modes can propagate in addition to the TEM mode. Multi-mode propagation can occur with a transparent conductor core (internal electrode) or a transparent conductor located between the internal electrode and the external electrode (in addition to the photovoltaic material). The transparent conductor can have a diameter smaller or larger than the light wavelength, so that light can enter directly in addition to indirectly via an antenna. The transparent conductor may have a nanoscale-thickness photovoltaic material on one or both sides. For multi-mode propagation, the overall inter-electrode spacing in the cometal structure should be approximately the same as the light wavelength.

In a photovoltaic apparatus, light energy is absorbed by the photovoltaic semiconductor medium and transferred to electrons in the semiconductor valence band. This increases the energy of the electrons, promoting them to the semiconductor conduction band, where they become mobile. Each electron that has been promoted to the conduction band leaves behind a hole in the valence band. The hole can be considered a positively-charged entity, in contrast to the electron's negative electrical charge, and the hole is also mobile. Once this electron-hole pair has been generated, each of the electron and the hole must be harvested, by migrating to a metal electrode. The migration happens under the influence of an electric field, with the holes moving in the direction of the field, the electrons against the field.

An electric field in an apparatus of the presently disclosed embodiments can be created in several ways including a Schottky barrier, a p-n junction and a p-i-n junction. A Schottky barrier is a metal-semiconductor junction that has rectifying characteristics, suitable for use as a diode. Most metal-semiconductor junctions intrinsically form a Schottky barrier. By forming two Schottky barriers, one at each metal-semiconductor junction in the cometal structure, an appropriate electric field is established. A p-n junction is formed by combining n-type semiconductors and p-type semiconductors together in close contact. A p-n junction also establishes an electric field. A p-i-n junction (p-type semiconductor, intrinsic semiconductor, n-type semiconductor) is a junction diode with a wide, undoped intrinsic semiconductor region between p-type semiconductor and n-type semiconductor regions. For solar cells, the p- and n-regions are thin relative to the intrinsic semiconductor region, and are present to establish the electric field.

In an embodiment, the photovoltaic material contacts a portion of the electrically conducting core. A substrate may support the plurality of nanoscale coaxial structures. In an embodiment, the photovoltaic material contains a p-n junction comprised of photovoltaic semiconductors. In an embodiment, the photovoltaic material contains a p-i-n junction formed of a p-type semiconductor layer, an intrinsic photovoltaic semiconductor layer and an n-type semiconductor layer. In an embodiment, a transparent conductor is located between the electrically conducting core and the outer electrical conductor layer.

In an embodiment, the plurality of coaxial structures are connected in series, resulting in a total voltage being a sum of voltages photo-generated by each coaxial structure. In an embodiment, the plurality of coaxial structures are connected in parallel, resulting in a total voltage between a minimum and a maximum of the voltages photo-generated by each cometal structure.

The visual neuroprosthetic devices of the presently disclosed embodiments may receive incident light in the form of infrared radiation. The devices may therefore be used for military purposes, such as: target acquisition, surveillance, homing and tracking.

A method of visual perception includes providing a visual neuroprosthetic device comprising an array of nanoscale waveguides, each nanoscale waveguide in the array having a photovoltaic material located between an internal conductor and an external conductor; implanting the visual neuroprosthetic device into an eye by engaging the device with a retina; receiving incident light on the array of nanoscale waveguides of the visual neuroprosthetic device; propagating the incident light through the array of nanoscale waveguides of the visual neuroprosthetic device; converting the incident light into an electrical neural signal; transferring the electrical neural signal to cells of the retina; and sending the electrical neural signal to a brain to create a visual image. The visual neuroprosthetic device may be implanted with standard eye surgery techniques.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A visual neuroprosthetic device comprising an array of nanoscale waveguides disposed on a substrate, each nanoscale waveguide in the array having a photovoltaic material located between an internal conductor and an external conductor, wherein each nanoscale waveguide receives, propagates, and converts incident light into electrical neural signals, and wherein a site density of the nanoscale waveguides on the substrate is the same as or greater than the site density of photoreceptors in the human retina.

2. The visual neuroprosthetic device of claim 1 wherein the internal conductor acts as an optical antenna with an impedance matched transmission line.

3. The visual neuroprosthetic device of claim 1 wherein each nanoscale waveguide in the array has a coaxial configuration.

4. The visual neuroprosthetic device of claim 1 further comprising a transparent substrate supporting the array of nanoscale waveguides.

5. The visual neuroprosthetic device of claim 1 further comprising a nontransparent substrate supporting the array of nanoscale waveguides.

6. The visual neuroprosthetic device of claim 1 further comprising a flexible substrate supporting the array of nanoscale waveguides.

7. The visual neuroprosthetic device of claim 1 further comprising a nonflexible substrate supporting the array of nanoscale waveguides.

8. The visual neuroprosthetic device of claim 1 further comprising a mechanical stabilizing film surrounding the array of nanoscale waveguides.

9. The visual neuroprosthetic device of claim 1 wherein the array of nanoscale waveguides engage and communicate with a retina of an eye.

10. The visual neuroprosthetic device of claim 1 wherein the array of nanoscale waveguides transfer the converted electrical neural signals to cells within a retina of an eye.

11. The visual neuroprosthetic device of claim 10 wherein the transferred signals travel through the cells of the retina and to fibers of the optic nerve to a brain to form a visual image.

12. The visual neuroprosthetic device of claim 1 wherein the incident light is a visible light.

13. The visual neuroprosthetic device of claim 1 wherein the incident light is an infrared light.

14. A visual neuroprosthetic device comprising a substrate; and an array of coaxial nanoscale waveguides disposed on the substrate, each nanoscale waveguide in the array having a photovoltaic material located between an internal conductor and an external conductor, wherein each nanoscale waveguide converts incident light into electrical neural signals, and wherein a site density of the nanoscale waveguides on the substrate is the same as or greater than the site density of photoreceptors in the human retina.

15. The visual neuroprosthetic device of claim 14 wherein the internal conductor acts as an optical antenna with an impedance matched transmission line.

16. The visual neuroprosthetic device of claim 14 further comprising a substrate supporting the array of nanoscale waveguides.

17. The visual neuroprosthetic device of claim 14 wherein the nanoscale waveguides are configured to engage and communicate with a retina of an eye.

18. The visual neuroprosthetic device of claim 14 wherein the array of nanoscale waveguides are configured to transfer the converted electrical neural signals to cells within a retina of an eye.

19. The visual neuroprosthetic device of claim 14 further comprising a mechanical stabilizing film surrounding the array of nanoscale waveguides.

20. A visual neuroprosthetic device comprising:
a substrate having two or more zones, including at least a first zone and a second zone;
a first array of first nanoscale waveguides disposed over a first zone of the substrate, the first nanoscale waveguides having a first diameter; and
a second array of second nanoscale waveguides disposed over a second zone of the substrate, the second nanoscale waveguides having a second diameter different than the first diameter,
wherein each nanoscale waveguide of the first nanoscale waveguides and the second nanoscale waveguides has a photovoltaic material located between an internal conductor and an external conductor such that each nanoscale waveguide converts incident light into electrical neural signals.

21. The visual neuroprosthetic device of claim 20 wherein the internal conductor acts as an optical antenna with an impedance matched transmission line.

22. The visual neuroprosthetic device of claim 20 wherein each nanoscale waveguide in the array has a coaxial configuration.

23. The visual neuroprosthetic device of claim 20 wherein the nanoscale waveguides are configured to engage and communicate with a retina of an eye.

24. The visual neuroprosthetic device of claim 20 wherein the first zone has a first site density of nanoscale waveguides and the second zone has a second site density of nanoscale waveguides different than the first site density.

25. The visual neuroprosthetic device of claim 20 wherein the first and second nanoscale waveguides are configured to transfer the converted electrical neural signals to cells within a retina of an eye.

26. The visual neuroprosthetic device of claim 20 wherein the first diameter is larger than the second diameter.

* * * * *